United States Patent [19]

Funk et al.

[11] Patent Number: 5,502,248
[45] Date of Patent: Mar. 26, 1996

[54] PROCESS FOR CONCURRENT HYDROLYSIS OF ESTERS AND SEPARATION OF PRODUCTS USING A SIMULATED MOVING BED

[75] Inventors: Gregory A. Funk, Carol Stream; Hemant W. Dandekar; Simon H. Hobbs, both of Chicago, all of Ill.

[73] Assignee: UOP, Des Plaines, Ill.

[21] Appl. No.: 395,240

[22] Filed: Feb. 27, 1995

[51] Int. Cl.⁶ .................................................. C07B 53/00
[52] U.S. Cl. .................................... 562/606; 562/483
[58] Field of Search .............................................. 562/606

[56] References Cited

U.S. PATENT DOCUMENTS

| | | | |
|---|---|---|---|
| 2,511,467 | 6/1950 | Gresham | 562/606 |
| 2,984,688 | 5/1961 | Sixt | 562/606 |
| 4,008,291 | 2/1977 | Zabransky et al. | 260/283 |
| 4,028,430 | 6/1977 | Stine et al. | 260/683 |
| 4,091,039 | 5/1978 | Scheibel | 562/606 |
| 4,185,027 | 1/1980 | Logan | 562/606 |
| 4,218,386 | 8/1980 | Logan | 562/606 |
| 4,323,702 | 4/1982 | Kawabata | 562/485 |
| 4,358,609 | 11/1982 | Hardy | 562/606 |
| 4,822,913 | 4/1989 | Hagen | 562/598 |

FOREIGN PATENT DOCUMENTS

| | | |
|---|---|---|
| 685802 | 3/1965 | Italy . |
| 3144504 | 12/1978 | Japan . |
| 93/08150 | 4/1993 | WIPO . |

OTHER PUBLICATIONS

Sardin, M., Schweich, D., Villermaux, J., In *Preparative and Production Scale Chromatography;* Ganetsos, G., Barker, P. E., Eds.; Chromatographic Science Series, vol. 61; Marcel Dekker: New York, 1993; Chapter 20, pp. 511–516.

Ray, A.; Tonkovich, A. L.; Aris, R.; Carr, R. W.; *Chem. Eng. Sci.*, 1990, vol. 45, No. 8, pp. 2431–2437.

*Primary Examiner*—Paul J. Killos
*Attorney, Agent, or Firm*—Thomas K. McBride; Eugene I. Snyder; Maryann Maas

[57] ABSTRACT

A process for the continuous hydrolysis of esters containing from 2 to about 16 carbon atoms to form at least one alcohol and at least one carboxylic acid and the concurrent separation of the hydrolysis products has been developed. The process uses a solid bed which acts as a catalyst for hydrolysis and as an adsorbent for at least one class of the products. The process operates in the simulated moving bed mode. A specific embodiment of the invention is one where the simulated moving bed is a homogeneous mixture of at least one solid effective as a hydrolysis catalyst and at least one solid effective as an alcohol or carboxylic acid adsorbent. Another specific embodiment is one where the simulated moving bed is a strongly acidic macroreticular polymeric resin effective both as a hydrolysis catalyst and as an adsorbent for at least one hydrolysis product.

30 Claims, 3 Drawing Sheets

2

PROCESS FOR CONCURRENT HYDROLYSIS OF ESTERS AND SEPARATION OF PRODUCTS USING A SIMULATED MOVING BED

BACKGROUND OF THE INVENTION

Many reactions of commercial importance, including the hydrolysis of esters, are limited by thermodynamic equilibrium, and historical techniques of performing these reactions involved two sequential steps. The first step was the reaction step which ceased when equilibrium was reached. Generally, upon reaching equilibrium, both reactants and products were present in one mixture, therefore necessitating a second step to separate the product of interest from the unconverted reactants which may be recycled to the reactor. The obvious drawbacks to the historical approach are the costs associated with a two-step approach, often involving several reactors and separators, and the equilibrium-imposed limitation on the quantity of product formed.

A technique which has been investigated and applied to equilibrium-limited reactions in order to shift equilibria to favor the yield of products is the use of reactive chromatography. Reactive chromatography has been described as a technique employing a chromatographic and a reactor system that is used both to react components and to concurrently separate one or more of the products that are formed. Several different operating configurations such as a fixed bed with pressure swing or cylindrical annular bed with rotating feed input source, a countercurrent moving bed, and a countercurrent simulated moving bed have been explored. See generally, Vaporciyan, G. G.; Kadlec, R. H. *AIChE J.* 1987, 33(8), 1334–1343; Fish, B. B.; Carr, R. W. *Chem. Eng. Sci.* 1989, 44, 1773–1783; and Carr, R. W. In *Preparative and Production Scale Chromatography;* Ganetsos, G., Barker, P. E., Eds.; Chromatographic Science Series Vol. 61; Marcel Dekker: New York, 1993; Chapter 18.

The hydrolysis of diesters and the concurrent separation of the products has been investigated using a fixed bed chromatographic reactor. See, Sardin, M.; Schweich, D.; Villermaux, J. In *Preparative and Production Scale Chromatography;* Ganetsos, G., Barker, P. E., Eds.; Chromatographic Science Series Vol. 61; Marcel Dekker: New York, 1993; Chapter 20, pp. 511–516. In this reference, the stated goal of the work was to increase the yield of one of two competing reactions. The chromatographic reactor used in this reference was a column packed with activated charcoal, and the feed contained ethylene glycol diacetate and sodium hydroxide in a carrier of 2.5% ethanol in water. The glycol diacetate reacts with the sodium hydroxide to form glycol monoacetate and sodium acetate and the glycol monoacetate also further reacts with the sodium hydroxide to form glycol and sodium acetate. The stated goal of the experimentation was to increase the yield of the glycol monoacetate; however, this goal was not attained.

Other reactions and separations, such as mesitylene hydrogenation, have been accomplished using simulated moving beds. See, Ray, A.; Tonkovich, A. L.; Aris, R.; Carr R. W. *Chem Eng. Sci.,* 1990, Vol. 45 No. 8, pp 2431–2437. Some applications of simulated moving beds have focused on simultaneous reaction and catalyst regeneration. In U.S. Pat. Nos. 4,028,430 and 4,008,291 an alkylation reaction and catalyst regeneration through the removal of adsorbed water were disclosed. However, applicants are the first to realize that the simulated moving bed technique combined with reactive chromatography can be successfully applied to the hydrolysis of esters to form at least one alcohol and at least one carboxylic acid and specifically applied to the hydrolysis of methyl acetate to form methanol and ethanoic acid. Applying simulated moving bed technology to reactive chromatography for ester hydrolysis will achieve high amounts of conversion with less process equipment as compared to fixed-bed systems. In addition, the disclosed invention eliminates costs associated with the recycle of unconverted reactants which are common in other processes.

SUMMARY OF THE INVENTION

The purpose of this invention is to provide a process for the continuous hydrolysis of at least one ester containing from about 2 to about 16 carbon atoms to produce at least one alcohol and at least one carboxylic acid through contacting the ester with a simulated moving bed acting as a catalyst for hydrolysis and an adsorbent for at least one of the product classes, i.e., alcohol or carboxylic acid, and desorbing the separated adsorbed product class using a desorbent. A specific embodiment of the invention is one where the simulated moving bed is a homogeneous mixture of at least one solid effective as a hydrolysis catalyst and at least one solid effective as an alcohol or carboxylic acid adsorbent. Another specific embodiment is one where the simulated moving bed is a strongly acidic macroreticular polymeric resin effective both as a hydrolysis catalyst and as an adsorbent for at least one class of hydrolysis product. Another yet more specific embodiment is one where the solid, effective both as a catalyst and as an adsorbent, is selected from the group consisting of Amberlyst™-15, Amberlyst™-18, Amberlyst™-35 and Amberlyst™-36. A still more specific embodiment of the invention is one where methyl acetate is hydrolyzed to form methanol and ethanoic acid. Another more specific embodiment of the invention is one where methyl acetate is hydrolyzed to form methanol and ethanoic acid, and the simulated moving bed is Amberlyst™-36.

BRIEF DESCRIPTION OF THE DRAWINGS

FIG. 1 has been simplified by the deletion of a large number of pieces of apparatus customarily employed on a process of this nature which are not specifically required to illustrate the performance of the subject invention.

DETAILED DESCRIPTION OF THE INVENTION

Figure 1:
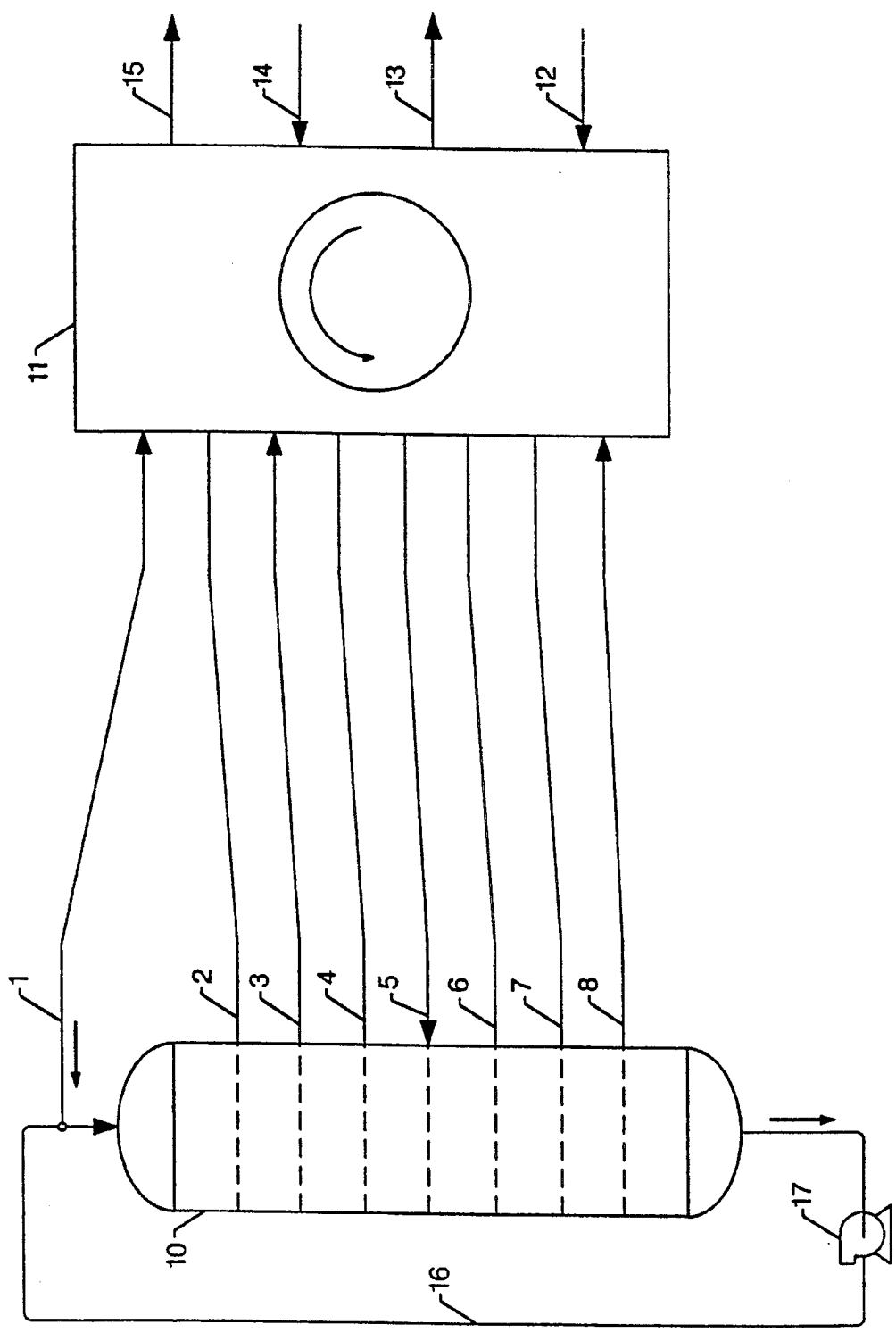
FIG. 1 is a schematic representation of a generic commercial simulated moving catalyst and adsorbent bed process, modified and operated in accordance with the process of this invention.

The invention is a process for the continuous hydrolysis of at least one ester to form at least one alcohol and at least one carboxylic acid using a simulated moving bed to effect reactive chromatography, i.e., a process where a simulated moving bed both catalyzes the hydrolysis reaction and effects the separation of hydrolysis products. In general terms, the reactants, at least one ester and water, are contacted with a simulated moving bed of a solid or a mixture of solids. The bed is both effective to catalyze hydrolysis and to separate the hydrolysis products, at least one alcohol and at least one carboxylic acid, through adsorption of at least one class of product. Once separated, the adsorbed product class is desorbed by a desorbent and the now separated alcohol(s) and carboxylic acid(s) are continuously removed from the simulated moving bed and recovered. Both reactive chromatography and simulated moving bed technology are known in the art, and a general discussion of these technologies may be found in Mowry, J. R. In *Handbook of Petroleum Refining Processes;* Meyers, R. A. Ed.; McGraw-Hill: New York, 1986; pp 8-79 to 8-99 for the simulated moving bed technique; and *Preparative and Production Scale Chromatography;* Ganetsos, G., Barker, P. E., Eds.; Chromatographic Science Series Vol. 61; Marcel Dekker: New York, 1993; Chapters 16–21 for reactive chromatography. Applicants have realized that these technologies may be effectively applied to the hydrolysis reaction of at least one ester to form at least one alcohol and one carboxylic acid, and the details of reactive chromatography and simulated moving bed technique as applied to the instant invention are supplied below.

The subject invention may be successfully applied to various hydrolysis reactions where at least one ester and water are reacted to form at least one alcohol and at least one carboxylic acid. Suitable esters include those containing from about 2 to about 16 carbon atoms, where the alcohol portion of the ester contains from 1 to 15 carbon atoms, and the carboxylic acid portion of the ester contains from 1 to 15 carbon atoms. Examples of suitable alcohol portions of the ester include methanol, ethanol, propanol, butanol, pentanol, hexanol, heptanol, octanol, nonanol, decanol, undecanol, dodecanol, tridecanol, tetradecanol, pentadecanol, 1,2-ethanediol, 1,2-propanediol, and 1,2,3-propanetriol. Examples of suitable carboxylic acid portions of the ester include methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, and pentadecanoic acid. Specific example of suitable esters include, methyl acetate, ethyl acetate, propyl acetate, butyl acetate, 2-butyl acetate, methyl formate, ethyl formate, 2-butyl formate, 2-ethyl-1-hexyl acetate, benzyl acetate, methyl propionate, ethyl propionate, propyl propionate, butyl propionate, 2-pentyl propionate, benzyl propionate, 1-methyl-nonyl ethanoate, 1-ethyl-decyl ethanoate, and 1-methyl-dodecyl propanoate.

The alcohols formed may contain from about 1 to about 15 carbon atoms. General examples include those alcohols listed above and specific examples of such alcohols include methanol, ethanol, 1-propanol, 2-propanol, 1-butanol, 2-butanol, cyclopentanol, cyclohexanol, benzyl alcohol, 1-phenylethanol, 2-phenylethanol, 2-methyl-2-propanol, 2-methyl-1-propanol, 2-ethyl-1-hexanol, phenol, 2-methylphenol, 3-methylphenol, 4-methylphenol, 1,2-ethanediol, 1,2-propanediol, 1,2,3-propanetriol, 2-decanol, 2-tridecanol, and 3-dodecanol. Similarly, the carboxylic acids formed may contain from about 1 to about 15 carbon atoms. General examples include those carboxylic acids listed above and specific examples are methanoic acid, ethanoic acid, propanoic acid, butanoic acid, pentanoic acid, hexanoic acid, octanoic acid, decanoic acid, phenylacetic acid, benzenecarboxylic acid, 2-methylbenzenecarboxylic acid, 3-methylbenzenecarboxylic acid, 4-methylbenzenecarboxylic acid, and cyclohexanecarboxylic acid. Of course, which alcohol and carboxylic acid is formed depends upon the ester hydrolyzed, and the sum of the carbon atoms of a product alcohol and corresponding carboxylic acid is equal to that of the parent ester.

Some examples of specific hydrolysis reactions which may be performed in the present invention are: hydrolyzing methyl acetate to form methanol and ethanoic acid; hydrolyzing ethyl acetate to form ethanol and ethanoic acid; hydrolyzing propyl acetate to form propanol and ethanoic acid; hydrolyzing butyl acetate to form butanol and ethanoic acid; hydrolyzing 2-butyl acetate to form 2-butanol and ethanoic acid; hydrolyzing methyl formate to form methanol and methanoic acid; hydrolyzing ethyl formate to form ethanol and methanoic acid; hydrolyzing 2-butyl formate to form 2-butanol and methanoic acid; hydrolyzing 2-ethyl-1-hexyl acetate to form 2-ethyl-1-hexanol and ethanoic acid; hydrolyzing benzyl acetate to form benzyl alcohol and ethanoic acid; hydrolyzing methyl propionate to form methanol and propanoic acid; hydrolyzing ethyl propionate to form ethanol and propanoic acid; hydrolyzing propyl propionate to form propanol and propanoic acid; hydrolyzing butyl propionate to form butanol and propanoic acid; hydrolyzing 2-pentyl propionate to form 2-pentanol and propanoic acid; hydrolyzing benzyl propionate to form benzyl alcohol and propanoic acid; hydrolyzing 1-methyl-nonyl ethanoate to form 2-decanol and ethanoic acid; hydrolyzing 1-ethyl-decyl ethanoate to form 3-dodecanol and ethanoic acid; and hydrolyzing 1-methyl-dodecyl propanoate to form 2-tridecanol and propanoic acid.

Reactive chromatography requires that the desired reaction and the separation of the products occur concurrently. Therefore, the simulated moving bed of the present invention must perform dual functions. The solid or mixture of solids forming the simulated moving bed must be effective as a catalyst to catalyze the hydrolysis reaction and also must be effective as an adsorbent which preferentially retains at least one class of the hydrolysis products in order to separate it from the other class of product. When the reactants enter the bed and contact the solid or mixture of solids, the hydrolysis reaction is catalyzed and at least one alcohol and at least one carboxylic acid is formed. The hydrolysis reaction primarily takes place in the portion of the solid bed adjacent to and immediately downstream, in the direction of the fluid flow, of the introduction point of the feed, which contains at least one ester. Since the solid or mixture of solids is also effective as an adsorbent for one of either the alcohol or the carboxylic acid, the products begin to undergo separation immediately upon being formed. The product which is less strongly adsorbed by the adsorbent is carried with the liquid flow, and the product which is strongly adsorbed by the adsorbent is carried countercurrently with the simulated movement of the solids. The migration of the two products in opposite directions results in one region richer in alcohol and the other region richer in carboxylic acid. Once separated, the product that was carried by the liquid flow is removed from its region by a liquid stream. Concurrently, the product carried by the adsorbent is desorbed at its region by the introduction of a liquid desorbent and removed from the bed by a second liquid stream. The process operates continuously with the reactants being introduced, the hydrolysis being catalyzed, and the products being separated and removed, thereby allowing the hydrolysis reaction to continue. Due to the continuous separation and removal of the products, the thermodynamic equilibrium characteristic of a static system is no longer a limiting factor, resulting in a greater yield. As a result, external recycle of unconverted reactants is greatly reduced or eliminated.

As previously discussed, the simulated moving bed is made up of particulate solids or a mixture of particulate solids which are effective to both catalyze the hydrolysis reaction and to separate the hydrolysis products. A wide variety of solid catalysts and adsorbents are available, and each particular hydrolysis application may require a different solid or combination of solids. Where one solid is used, the solid must sufficiently perform both the catalyst function and the adsorbent function. For example, both the hydrolysis of methyl acetate to form methanol and ethanoic acid and the concurrent separation of the methanol and ethanoic acid may be sufficiently accomplished by a strongly acidic cation exchange resin such as Amberlyst™-36, a macroreticular cation exchange polymeric resin manufactured by Rohm and Haas. Where two or more solids are used, they are used as a homogeneous mixture, and one solid may perform the catalysis function while the other performs the separation function. Examples of suitable catalysts include zeolite Beta, strongly acidic macroreticular polymeric resins and ZSM-5. Examples of suitable adsorbents include alumina, silica, molecular sieve carbon, activated carbon and weakly acidic macroreticular polymeric resins. The preferred solids are the strongly acidic macroreticular polymeric resins such as Amberlyst™-15, Amberlyst™-18, Amberlyst™-35 and Amberlyst™-36, which are capable of performing both the catalytic function and the adsorbent function. The above listed resins are manufactured by Rohm and Haas. Different hydrolysis and separations may require different ratios of catalyst to adsorbent or different catalyst and adsorbent combinations. Typically, the catalyst to adsorbent ratio is in the range of about 1:50 to about 50:1 with a preferred range of from about 1:10 to about 10:1.

The catalyst and adsorbent solid or mixture of solids, once chosen, is used in the process in the form of a simulated moving bed where the bed is held stationary, and the locations at which the various streams enter and leave the bed are periodically moved. The bed itself is usually a succession of fixed sub-beds, and different hydrolysis reactions may require differing numbers of sub-beds. The most commonly used range is from about 4 sub-beds to about 24 sub-beds, with the preferred range being from 8 to 24 sub-beds. The sub-beds may be housed in one chamber or in two or more interconnected chambers. The preferred design contains one chamber.

The shift in the locations of liquid input and output streams in the direction of the fluid flow through the bed simulates the movement of the solid bed in the opposite direction. Commercially, moving the locations of liquid input and output streams is accomplished by a fluid-directing device known generally as a rotary valve which works in conjunction with distributors located between the adsorbent sub-beds. The rotary valve accomplishes moving the input and output locations through first directing the liquid introduction or withdrawal lines to specific distributors located between the adsorbent sub-beds. After a predetermined time period called the step time, the rotary valve advances one index and redirects the liquid inputs and outputs to the distributors immediately adjacent and downstream of the previously used distributors. Each advancement of the rotary valve to a new valve position is generally called a valve step, and the completion of all the valve steps is called a valve cycle. The step time is uniform for each valve step in a valve cycle, and the valve cycle time ranges generally from about 15 minutes to about 3 hours.

The simulated moving bed is operated at pressures sufficient to sustain the feed, products and desorbent in the liquid phase, usually from about 1 to about 50 atm, and at temperatures from about 25° to about 200° C. Generally, for a given catalyst, the higher the temperature, the greater the rate of reaction and consequently the better the performance. However, other factors can affect the choice of operating temperatures such as: 1) the temperature stability of the catalyst and adsorbent solids contained in the simulated moving bed, 2) the effect of temperature on the adsorbent capacity, and 3) the effect of temperature on the solubility of the reactants. For example, where the ester is methyl acetate and the catalyst and adsorbent is Amberlyst™-36, a preferred range of operating temperatures is about 50° to about 150° C.

The principal liquid inputs and outputs of the simulated moving bed system consist of four streams: the desorbent, the feed, the extract, and the raffinate. Each stream flows into or out of the simulated moving bed at individual locations and at a particular flow rate which is independently controlled.

The desorbent, which is introduced to the simulated moving bed system, contains a liquid capable of displacing a selectively adsorbed reaction product from the bed. The most preferred desorbent liquid is a mixture containing at least water. Of course, water is a reactant necessary for the hydrolysis, but it can also perform as a desorbent. For example, water may be used both as the desorbent and as a reactant in the hydrolysis of methyl acetate to form ethanoic acid and methanol. However, it is also necessary that the desorbent be miscible with the reactants and products. Therefore, when using water as the desorbent, an additional solvent is often necessary both to modify the desorbing strength of the water and to aid miscibility and ensure that the system remains in one phase. Furthermore, the solvent may be chosen to act as a distillation entrainer to help break azeotropes which may form. For example, where the ester is ethyl acetate, an azeotrope may form between the products ethanoic acid and water or between ethyl acetate and ethanol. Similarly, where the ester is methyl acetate, an azeotrope may form between the products ethanoic acid and water or between methyl acetate and methanol. Examples of suitable desorbents or solvents which are not reactants include diethylene glycol methyl ether and ethylene glycol dimethyl ether. It is not necessary to have a solvent in every application. The solvent, where necessary, is generally present in an amount ranging from about 5 mass % to about 90 mass % of the desorbent mixture.

The feed, which is introduced to the simulated moving bed system, contains at least one ester containing from 2 to about 16 carbon atoms which is to undergo catalytic hydrolysis to form at least one alcohol and at least one carboxylic acid. Typical examples of acceptable esters, alcohols and carboxylic acids were discussed above. If the desorbent being used is water, it is not necessary for the feed to contain water. What is necessary is that the feed and desorbent collectively contain all required reactants, including water and at least one ester.

The extract and the raffinate are both withdrawn from the simulated moving bed system. The extract contains the separated hydrolysis product which was selectively adsorbed by the bed and then desorbed by the desorbent liquid, and the raffinate contains the other reaction product which was less strongly adsorbed by the bed. For example, in the hydrolysis of methyl acetate to form methanol and ethanoic acid using Amberlyst™-36, the methanol is selectively adsorbed by the bed and is therefore found in the extract while the ethanoic acid is only slightly adsorbed by the bed and is found in the raffinate. Each stream is a mixture of the respective product and desorbent. The product, if desired, may be recovered from the desorbent through conventional means such as fractionation, and the desorbent may be recycled. Each of these streams may also contain unreacted ester. Although not necessary, in order to simplify recovery of the hydrolysis products and to simplify the recycle of the desorbent, it is preferred that substantially all of the ester be converted in the hydrolysis.

There also may be associated flush streams introduced to and withdrawn from the simulated moving bed and a pumparound stream. Although functionally the simulated moving bed as a whole does not have a top or a bottom, the chamber housing the bed has a physical top and bottom. The pumparound stream conducts the liquid exiting the physical bottom of the chamber back up to reenter the physical top of the chamber. In an eight sub-bed example, the pumparound stream would be the stream that conducts the effluent of sub-bed 8 from the physical bottom of the chamber to reenter sub-bed 1 at the physical top of the chamber.

Typically, in a commercial system, the four principal streams are spaced strategically throughout the simulated moving bed system and divide the sub-beds into four zones, each of which performs a different function. Zone I contains the sub-beds located between the feed input and the raffinate output, and the majority of the hydrolysis reaction and the adsorption of at least one hydrolysis product takes place in this zone. Zone II contains the sub-beds located between the extract output and the reactant input, and some of the hydrolysis reaction, the desorption of the less selectively adsorbed product, and the continued adsorption of the selectively adsorbed product, take place in this zone. Zone III contains the sub-beds located between the desorbent input and the extract output, and the selectively adsorbed reaction product is desorbed in this zone. The desorption may serve to regenerate the solid in addition to allowing the selectively adsorbed product to be collected. Finally, Zone IV contains the sub-beds located between the raffinate output and the desorbent input, and the purpose of this zone is to prevent the contamination or loss of the separated products.

Without intending any limitation on the scope of the present invention and as merely illustrative, this invention is explained below in specific terms as applied to one specific embodiment of the invention, the continuous hydrolysis of methyl acetate to form methanol and ethanoic acid using Amberlyst™-36 to effect both the hydrolysis and the separation of the products and using ethylene glycol dimethyl ether as a solvent. For ease of understanding, the process of the invention described below is limited to having eight sub-beds housed in one chamber. The necessary apparatus is first described and then the process of the invention as applied to the embodiment is discussed.

Referring now to the apparatus as illustrated in FIG. 1, distribution lines 1–8 are available to conduct liquid streams to or from the chamber 10. Chamber 10 houses eight sub-beds of Amberlyst™-36. The distribution lines connect with the simulated moving bed at locations between successive sub-beds and separate the simulated moving bed into four zones as described earlier. Distribution lines 1–8 are also connected to a rotary valve 11. Rotary valve 11 is further connected to line 12 which conducts the methyl acetate feed to the valve, line 13 which conducts raffinate, a mixture of ethanoic acid, water, and ethylene glycol dimethyl ether, away from the valve, line 14 which conducts desorbent, a mixture of water and ethylene glycol dimethyl ether, to the valve, and line 15 which conducts extract, a mixture of methanol, water and ethylene glycol dimethyl ether, away from the valve. Each of the lines 12–15 is provided with a flow rate sensor and flow control valve (not shown). Line 16 conducts the effluent, or pumparound stream, from the bottom of chamber 10 back to the top of chamber 10 and is equipped with a pump 17.

Using the described apparatus, the invention is performed as follows. The flow rates of each of lines 12–15 and the step time of rotary valve 11 may be first set to selected values based on the operator's experience. The starting position of the rotary valve is not important; for this illustration the starting position of the rotary valve is such that the desorbent is directed to chamber 10 through distribution line 1, the extract is directed from chamber 10 through distribution line 3, the feed is directed to chamber 10 through distribution line 5, and the raffinate is directed from chamber 10 through distribution line 8. When the step time has elapsed, rotary valve 11 advances one index and now directs the desorbent through distribution line 2, the extract through distribution line 4, the feed through distribution line 6, and the raffinate through distribution line 1. When the step time has again elapsed, the streams will again be directed to the next successive distribution line in the direction of the flow, and the continued progression of the streams will simulate the movement of the solid bed in the countercurrent direction.

For ease of understanding, the operation is described with rotary valve 11 in the starting position as above. When the feed containing the methyl acetate reactant, conducted in distribution line 5, enters the simulated moving bed chamber 10 and contacts the Amberlyst™-36 and the water from the desorbent mixture, the hydrolysis reaction is catalyzed, and methanol and ethanoic acid are formed. The methyl acetate and some of the water are converted. The ethanoic acid, which is weakly absorbed by the Amberlyst™-36, is carried with the fluid flow and withdrawn from the bed in the raffinate stream conducted in distribution line 8. The methanol, which is absorbed by the Amberlyst™-36, is retained by the solid bed in its countercurrent simulated movement thereby being separated from the ethanoic acid. The methanol is desorbed from the Amberlyst™-36 by the desorbent which is conducted to the bed through distribution line 1. The methanol is withdrawn from the simulated moving bed chamber 10 in the extract stream conducted in distribution line 3. Since the raffinate and the extract both contain water and ethylene glycol dimethyl ether, each stream is treated downstream in a fractionator (not shown) to remove and recycle the water and ethylene glycol dimethyl ether. Since an azeotrope is formed between the methyl acetate and the methanol, further treatment such as extractive distillation may be required.

It must be emphasized that the above description is merely illustrative of a preferred embodiment and is not intended as an undue limitation on the generally broad scope of the invention. Moreover, while the description is narrow in scope, one skilled in the art will understand how to extrapolate to the broader scope of the invention. For example, operation of the invention where the sub-beds of the simulated moving bed may be housed in two or more interconnected chambers can be readily extrapolated from the foregoing description. Similarly, one skilled in the art would understand that the simulated moving bed may also be a homogeneous mixture of two or more solids, or that the desorbent and the feed may have other compositions. Furthermore, the optimum number of sub-beds, the optimum cycle time, and the optimum flow rates would be readily determined by one skilled in the art.

The examples below are not intended as a limitation on the scope of the present invention, and are merely illustrative of the reaction and separation performance. The first and second examples employed the commonly used pulse test which has been frequently used to evaluate various adsorbents or catalysts with particular solutions and desorbents to measure adsorption or reaction characteristics. The apparatus for this test consisted of a catalyst and adsorbent chamber of approximately 70 cc volume having inlet and outlet portions at opposite ends of the chamber. The chamber was maintained at constant temperature and pressure. Analytical instrumentation was attached to the outlet line of the chamber to measure the concentration of one or more components eluting from the chamber. To perform the test, the catalyst and adsorbent were placed in the chamber and filled to equilibrium with the desorbent by passing the desorbent through the adsorbent chamber at approximately one liquid hourly space velocity. At a convenient time, a 2 mL pulse of a solution containing at least the ester to be hydrolyzed and then separated was injected, and then the desorbent flow was resumed. The components were eluted as in a liquid-solid chromatographic operation and could be analyzed on-line, or samples could be periodically collected and analyzed separately. Catalyst and adsorbent performance may be rated from the results of this test. The pulse test described above, and used in these examples, is similar to, but at a reduced scale, of the commonly used pulse test described in, for example, U.S. Pat. Nos. 5,220,102 and 3,855,333.

EXAMPLE 1

Figure 2:
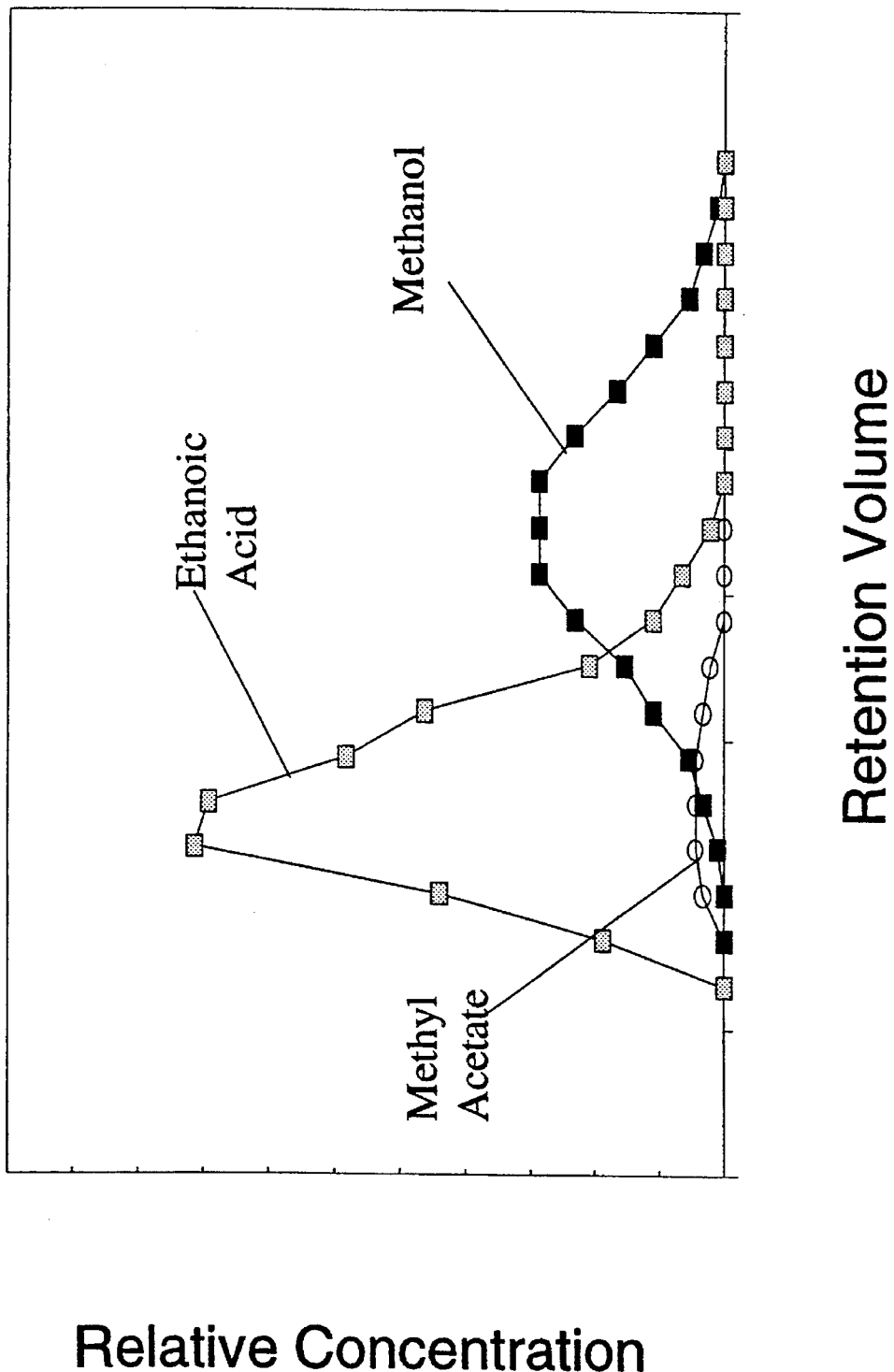
FIG. 2 is the chromatographic plot of the conversion and separation of a mixture of methyl acetate, water, and ethylene glycol dimethyl ether, using Amberlyst™-36 as both the catalyst and the adsorbent as conducted in Example 1.

A pulse test, as described above, was performed using a catalyst and adsorbent chamber, having inlet and outlet portions at opposite ends, which contained 70 cc of Amberlyst™-36. The chamber was maintained at 100° C., and 150 psi. An on-line gas chromatograph was used to determine the composition of the effluent stream leaving the catalyst and adsorbent chamber. The desorbent, containing a mixture of 80% water and 20% ethylene glycol dimethyl ether, was passed through the adsorbent material at a flow rate of approximately one liquid hourly space velocity. At a particular time after equilibrium had been established, a 2 mL pulse of a mixture of 20% methyl acetate, 20% water, and 60% ethylene glycol dimethyl ether was injected. Desorbent flow was resumed, and the effluent was analyzed periodically by the on-line gas chromatograph. As FIG. 2 illustrates, most of the methyl acetate was converted to ethanoic acid and methanol. Furthermore, the ethanoic acid and methanol were separated, as demonstrated by the resolution between the ethanoic acid peak, which eluted first, and the methanol peak, which eluted second.

EXAMPLE 2

Figure 3:
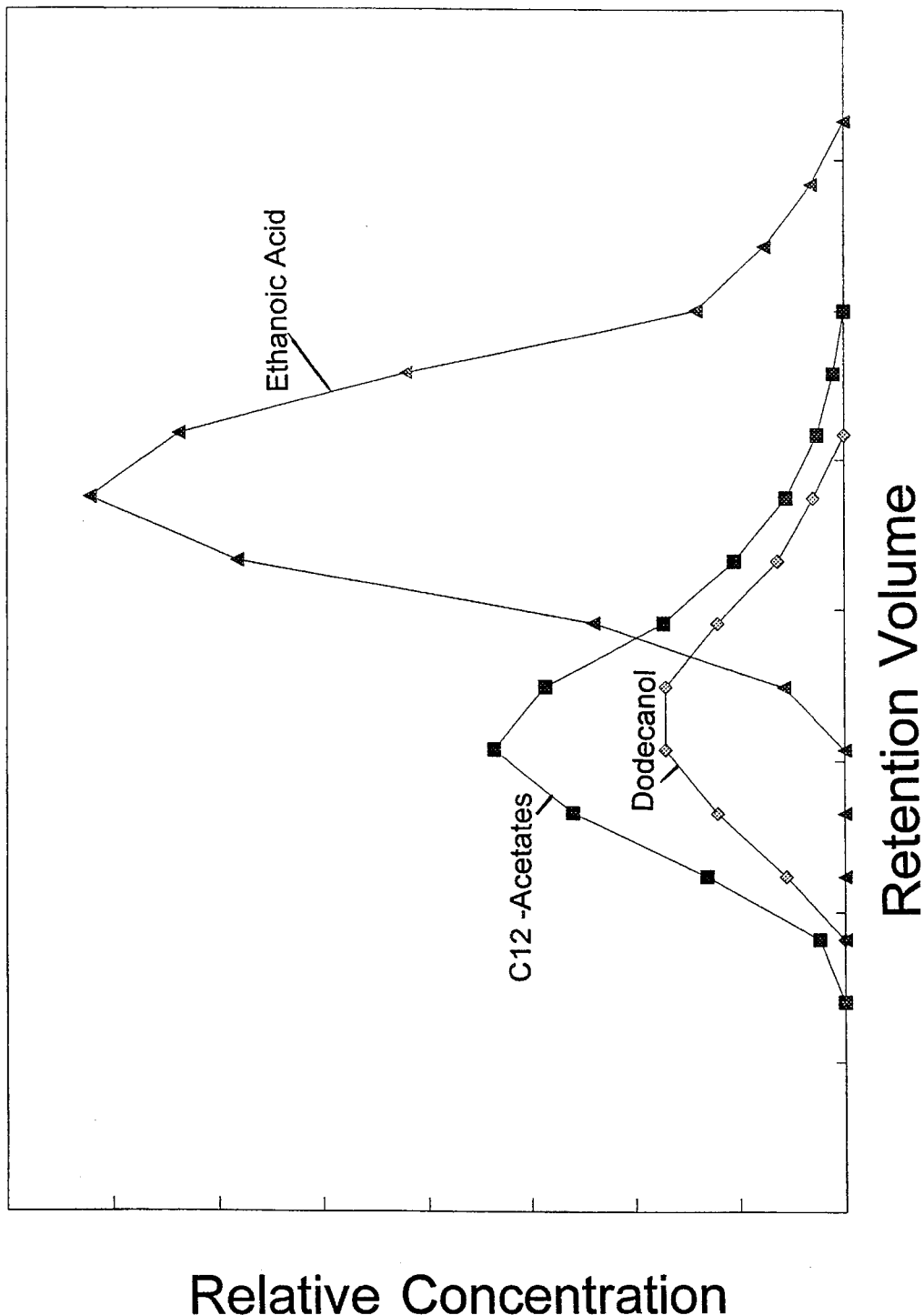
FIG. 3 is the chromatographic plot of the separation of a mixture of 56 mass % ethanoic acid, 18 mass % dodecanols, 15 mass % $C_{12}$ acetates and 11 mass % 2-methoxyethyl ether, using Amberlyst™-36 as both the catalyst and the adsorbent as conducted in Example 2.

A pulse test, as described above, was performed to primarily demonstrate the separation of product alcohols having a high number of carbon atoms from carboxylic acids, although some concurrent ester hydrolysis occurred. The pulse test used a catalyst and adsorbent chamber, having inlet and outlet portions at opposite ends, which contained 70 cc of Amberlyst™-36. The chamber was maintained at 120° C. and 250 psi. An on-line gas chromatograph was used to determine the composition of the effluent stream leaving the catalyst and adsorbent chamber. The desorbent, containing a mixture of 15 mass % water and 85 mass % 2-methoxyethyl ether, was passed through the adsorbent material at a flow rate of approximately one liquid hourly space velocity. At a particular time after steady state had been established, a 2 mL pulse of a mixture of 56 mass % ethanoic acid, 18 mass % dodecanols, 15 mass % $C_{12}$ acetates and 11 mass % 2-methoxyethyl ether was injected. Desorbent flow was resumed, and the effluent was analyzed periodically by the on-line gas chromatograph. As FIG. 3 illustrates, the alcohols and carboxylic acid were separated under the conditions of the experiment, as demonstrated by the resolution between the dodecanol peak, which eluted first, and the ethanoic acid peak, which eluted second. By performing the reaction and separation in the simulated moving bed process described above, one can continuously remove the acetic acid product from the dodecanol product and thereby prevent back-reaction to overcome the equilibrium limitations of this reaction.

EXAMPLE 3

A pilot plant run was performed using a simulated moving bed to conduct the hydrolysis of methyl acetate to form ethanoic acid and methanol. The simulated moving bed contained 16 sub-beds, but no pumparound stream. The flow rates of the feed, desorbent, and extract streams were controlled using Waters pumps. The positions of the feed, desorbent, extract and raffinate were controlled by four separate valco valves. Samples were collected and analyzed on an HP5890 Gas Chromatograph equipped with a DB-17 column. The feed was HPLC grade methyl acetate obtained from Aldrich Chemical with a purity of greater then 99.8 mass %. The desorbent was a mixture of water and ethylene glycol dimethyl ether, with the ethylene glycol dimethyl ether being HPLC grade from Aldrich Chemical and having a purity of greater than 99.8 mass %. The solid performing both as a catalyst to effect hydrolysis and as an adsorbent to separate the hydrolysis products was Amberlyst™-36. The volume of Amberlyst™-36 used was 120 cc.

The two primary indicators of performance were the purity of the methanol in the extract stream and the conversion of the methyl acetate. The purity of methanol was calculated on a water and ethylene glycol dimethyl ether-free basis, and the conversion of the methyl acetate was calculated according to the formula:

$$\text{Conversion} = \frac{(F)(XF) - (E)(XE) - (R)(XR)}{(F)(XF)}$$

Where:
F=the flow rate of the feed in grams/hour
E=the flow rate of the extract in grams/hour
R=the flow rate of the raffinate in grams/hour
XF=the weight fraction of methyl acetate in the feed
XE=the weight fraction of methyl acetate in the extract
XR=the weight fraction of methyl acetate in the raffinate Several variables were investigated during the pilot plant run. For example. Applicants determined that when the cycle time was decreased from 2 hours to 1 hour, the conversion decreased from 95.5 mass % to 92 mass % at comparable purity. Also, at an operating temperature of 80° C., the performance obtained was 97% purity at 85% conversion, while at 100° C. the performance improved to 97% purity at 88% conversion. Similarly, by increasing desorbent strength by increasing the amount of water in the desorbent mixture from 20 mass % to 80 mass % improved the conversion from 59% to 85% at a purity of 94% or higher. Some of this improvement may be attributed to the shift in equilibrium due to a higher concentration of water in the system.

What is claimed is:

1. A liquid phase process for the continuous hydrolysis of esters containing from about 2 to about 16 carbon atoms with concurrent separation of hydrolysis products comprising:

a. continuously introducing a desorbent and a feed, which collectively comprise at least one ester and water, to a simulated moving bed of a solid or a mixture of solids effective to catalyze hydrolysis and to separate hydrolysis products by selective adsorption of at least one product;

b. hydrolyzing the ester(s) to form the hydrolysis products consisting of at least one alcohol and at least one carboxylic acid;

c. separating the alcohol(s) from the carboxylic acid(s) by selectively adsorbing at least one class of product on the solid or mixture of solids;

d. desorbing the selectively adsorbed class of product from the solid or mixture of solids using the desorbent; and e. collecting and recovering the separated alcohol(s) and carboxylic acid(s).

2. The process of claim 1 where the alcohol portion of the ester contain from 1 to about 15 carbon atoms.

3. The process of claim 1 where the alcohol portion of the ester is selected from the group consisting of methanol, ethanol, propanol, butanol, pentanol, hexanol, heptanol, octanol, nonanol, decanol, undecanol, dodecanol, tridecanol, tetradecanol, pentadecanol, 1,2-ethanediol, 1,2-propanediol, and 1,2,3-propanetriol.

4. The process of claim 1 where the carboxylic acid portion of the ester contains from 1 to about 15 carbon atoms.

5. The process of claim 1 where the carboxylic acid portion of the ester is selected from the group consisting of methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, and pentadecanoic acid.

6. The process of claim 1 where the simulated moving bed is a mixture of solids containing a solid effective as a hydrolysis catalyst selected from the group consisting of zeolite Beta, strongly acidic macroreticular polymeric resins and ZSM-5.

7. The process of claim 1 where the simulated moving bed is a mixture of solids containing a solid effective as an adsorbent selected from the group consisting of alumina, silica, molecular sieve carbon, activated carbon and weakly acidic resins.

8. The process of claim 1 where the simulated moving bed is a mixture of solids containing a solid effective as a hydrolysis catalyst and a solid effective as an adsorbent present in a ratio of from about 1:50 to about 50:1.

9. The process of claim 1 where the simulated moving bed is a mixture of solids containing a solid effective as a hydrolysis catalyst and a solid effective as an adsorbent present in a ratio of from about 1:10 to about 10:1.

10. The process of claim 1 where the simulated moving bed is a strongly acidic macroreticular polymeric resin which is effective as a catalyst and effective as an adsorbent.

11. The process of claim 10 where the strongly acidic macroreticular polymeric resin is selected from the group consisting of Amberlyst™-15, Amberlyst™-18, Amberlyst™-35 and Amberlyst™-36.

12. The process of claim 1 where the ester is methyl acetate, the alcohol is methanol, and the carboxylic acid is ethanoic acid.

13. The process of claim 12 where the solid effective as a catalyst and the solid effective as an alcohol or carboxylic acid adsorbent is Amberlyst™-36.

14. A liquid phase process for the continuous hydrolysis of esters containing from about 2 to about 16 carbon atoms with concurrent separation of hydrolysis products comprising:

a. continuously introducing a desorbent and a feed, which collectively comprise at least one ester, water, and at least one solvent, to a simulated moving bed of a solid or a mixture of solids effective to catalyze hydrolysis and to separate hydrolysis products by selective adsorption of at least one product;

b. hydrolyzing the ester(s) to form the hydrolysis products consisting of at least one alcohol and at least one carboxylic acid;

c. separating the alcohol(s) from the carboxylic acid(s) by selectively adsorbing at least one class of product on the solid or mixture of solids;

d. desorbing the selectively adsorbed class of product from the solid or mixture of solids using the desorbent; and e. collecting and recovering the separated alcohol(s) and carboxylic acid(s).

15. The process of claim 14 where said solvent is selected from the group consisting of diethylene glycol methyl ether, ethylene glycol dimethyl ether.

16. The process of claim 14 where said solvent is present in a mixture with said desorbent.

17. The process of claim 16 where said solvent and desorbent mixture contains from about 5 to about 95 mass % solvent.

18. The process of claim 14 where said desorbent is water which is present in a mixture containing from about 5 to about 95 mass % solvent.

19. The process of claim 14 where the alcohol portion of the ester contains from 1 to about 15 carbon atoms.

20. The process of claim 14 where the alcohol portion of the ester is selected from the group consisting of methanol, ethanol, propanol, butanol, pentanol, hexanol, heptanol, octanol, nonanol, decanol, undecanol, dodecanol, tridecanol, tetradecanol, pentadecanol, 1,2-ethanediol, 1,2-propanediol, and 1,2,3-propanetriol.

21. The process of claim 14 where the carboxylic acid(s) contain from 1 to about 15 carbon atoms.

22. The process of claim 14 where the carboxylic acid(s) are selected from the group consisting of methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, and pentadecanoic acid.

23. The process of claim 14 where the simulated moving bed is a mixture of solids containing a solid effective as a hydrolysis catalyst selected from the group consisting of zeolite Beta, strongly acidic macroreticular polymeric resins and ZSM-5.

24. The process of claim 14 where the simulated moving bed is a mixture of solids containing a solid effective as an adsorbent selected from the group consisting of alumina, silica, molecular sieve carbon, activated carbon and weakly acidic resins.

25. The process of claim 14 where the simulated moving bed is a mixture of solids containing a solid effective as a hydrolysis catalyst and a solid effective as an adsorbent present in a ratio of from about 1:50 to about 50:1.

26. The process of claim 14 where the simulated moving bed is a mixture of solids containing a solid effective as a hydrolysis catalyst and a solid effective as an adsorbent present in a ratio of from about 1:10 to about 10:1.

27. The process of claim 14 where the simulated moving bed is a strongly acidic macroreticular polymeric resin which is effective as a catalyst and effective as an adsorbent.

28. The process of claim 27 where the strongly acidic macroreticular polymeric resin is selected from the group consisting of Amberlyst™-15, Amberlyst™-18, Amberlyst™-35 and Amberlyst™-36.

29. The process of claim 14 where the ester is methyl acetate, the alcohol is methanol, and the carboxylic acid is ethanoic acid.

30. The process of claim 30 where the solid effective as a catalyst and the solid effective as an alcohol or carboxylic acid adsorbent is Amberlyst™-36.

* * * * *